(12) United States Patent
Lin et al.

(10) Patent No.: US 8,455,594 B2
(45) Date of Patent: Jun. 4, 2013

(54) PHOSPHOROUS FLAME RETARDANT AND APPLICATION THEREOF TO POLYMER

(75) Inventors: Jiang-Jen Lin, Taipei (TW); Yu-Min Chen, Taipei (TW); Yi-Lin Liao, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/567,936

(22) Filed: Aug. 6, 2012

(65) Prior Publication Data

US 2012/0302669 A1  Nov. 29, 2012

Related U.S. Application Data

(62) Division of application No. 12/751,987, filed on Mar. 31, 2010.

(30) Foreign Application Priority Data

Apr. 1, 2009 (TW) ................................ 98110942 A

(51) Int. Cl.
*C08F 230/02* (2006.01)
*C08G 8/28* (2006.01)
*C08L 61/00* (2006.01)
*C08L 63/00* (2006.01)
*C08L 79/02* (2006.01)

(52) U.S. Cl.
USPC ........... 525/512; 252/601; 252/609; 525/523; 523/466

(58) Field of Classification Search
USPC .................... 252/609, 601; 524/150; 525/512, 525/523; 523/466
See application file for complete search history.

(56) References Cited

FOREIGN PATENT DOCUMENTS

JP          2002-322189     * 11/2002

* cited by examiner

*Primary Examiner* — James J Seidleck
*Assistant Examiner* — Deve E Valdez
(74) *Attorney, Agent, or Firm* — Pai Patent & Trademark Law Firm; Chao-Chang David Pai

(57) ABSTRACT

A phosphorous flame retardant primarily includes hexachlorotriphosphazene (HCP) having poly(oxyalkylene)amine substitutes. The poly(oxyalkylene)amine includes at least two end groups. The phosphorous flame retardant can further include layered silicate clay. The layered silicate clay can be intercalated and modified with the poly(oxyalkylene)amine substitutes of HCP to effectively promote thermal stability. The flame retardant, phosphazene-poly(oxyalkylene)amine adducts, can be applied to a polymer. By the cross-linking between them, the flame-retarding property of the polymer can be improved. Also provided is a method for producing the flame retardant of phosphazene-poly(oxyalkylene)amine adducts and application thereof to a polymer.

18 Claims, 3 Drawing Sheets

PHOSPHOROUS FLAME RETARDANT AND APPLICATION THEREOF TO POLYMER

CROSS REFERENCE TO RELATED APPLICATIONS

The present application is a division of prior U.S. application Ser. No. 12/751,987 filed Mar. 31, 2010, entitled "PHOSPHOROUS FLAME RETARDANT AND APPLICATION THEREOF TO POLYMER". The prior U.S. Application claims priority of Taiwan Patent Application No. 098110942, filed on Apr. 1, 2009, the entirety of which is incorporated herein by reference.

BACKGROUND OF THE INVENTION

1. Field of the Invention

The present invention relates to a phosphorous flame retardant and a method for producing the same, and to an application of the flame retardant of phosphazene-poly(oxyalkylene)amine adducts to a polymer.

2. Related Prior Arts

Currently, to increase the flame retardant property of polymers, an inorganic or organic flame retardant is added therein. The inorganic flame retardant such as metal oxides or hydroxides, can be directly added; and the organic flame retardant such as compounds containing halogen, can be used in synthesis. However, the flame retardant containing halogen will produce corrosive and toxic hydrogen halide gases which perhaps generate dioxin at high temperatures. Therefore, the products containing halogen are forbidden in most areas or fields, and replaced with specific chemicals containing phosphorus. In Taiwan, it's important to develop environmentally friendly and economic flame retardants for application to electrical industries to replace conventional materials such as brominated epoxy.

The phosphorous flame retardant possesses the following characteristics:
a) it lowers the burning temperature because of dehydration of polymers;
b) when heated, phosphoric acid is released to carbonate polymers and form an inflammable carbon layer;
c) the released phosphoric acid can further dehydrate to form glass melt which can cover the burning object to prevent oxygen from entering and volatile matter from releasing; and
d) lower toxicity, better processing property, less smoke and good capacity with epoxy.

Therefore, properties of thermoplastic or thermosetting polymers could be improved by mixing with the above retardant during synthesis. To easily react with polymers, the retardant having —OH or —NH$_2$ functional group will be preferred and selected.

In addition to enhancing the flame retardant property of polymers, the phosphorous flame retardant of the present invention is expected to also improve their mechanical properties.

SUMMARY OF THE INVENTION

An object of the present invention is to provide an economic and environmentally friendly flame retardant based on phosphazene-poly(oxyalkylene)amine adducts and a method for producing the same so as to improve flame retardant and/or mechanical properties of polymers.

Another object of the present invention is to provide an economic and environmentally friendly flame retardant polymer and a method for producing the same.

In order to achieve the above objects, the flame retardant based on phosphazene-poly(oxyalkylene)amine adducts primarily includes hexachlorocyclotriphosphazene (HCP) having N poly(oxyalkylene)amine substitutes, wherein N is an integer 3~6, and the poly(oxyalkylene)amine includes at least two —NH$_2$ end groups.

The flame retardant based on phosphazene-poly(oxyalkylene)amine adducts is hereinafter also called as phosphorous flame retardant.

The phosphorous flame retardant of the present invention can further comprise a layered silicate clay which is intercalated and modified by the poly(oxyalkylene)amine substitutes of HCP. The cation exchanging equivalent (CEC) ratio of HCP and poly(oxyalkylene)amine to the layered silicate clay is about 0.2~1.0.

The present invention also provides a resin containing a flame retardant. The resin includes a polymer and the phosphorous flame retardant described in the above. There is a cross-linking structure between the phosphorous flame retardant and the polymer. Preferably, the phosphorus of HCP in the resin containing a flame retardant is 0.1~10 wt %.

The resin containing a flame retardant of the present invention can further comprise a layered silicate clay intercalated and modified by the poly(oxyalkylene)amine substitutes of HCP. The cation exchanging equivalent (CEC) ratio of HCP and poly(oxyalkylene)amine to the layered silicate clay is about 0.2~1.0; The layered silicate clay in the resin containing a flame retardant is about 0.1~15 wt %.

In the present invention, the method for producing the phosphorous flame retardant includes a step of: (1) mixing hexachlorocyclotriphosphazene (HCP), an alkaline and poly(oxyalkylene)amine in a solvent to perform a substitution reaction in which at least a chlorine of HCP is replaced with poly(oxyalkylene)amine. The poly(oxyalkylene)amine includes at least two —NH$_2$ end groups. The substitution reaction is controlled at 15~85° C.

The above mentioned poly(oxyalkylene)amine can be previously mixed with the solvent, and then slowly dropped into HCP dissolved in the solvent. The alkaline is then slowly dropped into the solution. Preferably, the mole ratio of the reactants HCP/poly(oxyalkylene)amine is 1/1~1/12. The substitution reaction is controlled at about 35~65° C. In the above, the solvent is tetrahydrofuran (THF); and the alkaline is triethylamine, pyridine or sodium hydroxide.

After the above step (1), the method can further comprise steps of: (2) mixing the product of step (1) with an acid to acidify the —NH$_2$ end groups; and (3) mixing the acidified product of step (2) with a layered silicate clay to perform an intercalation reaction.

The acid of step (2) is hydrochloric acid, nitric acid or sulfuric acid. The acidified —NH$_3^+$ and the layered silicate clay of step (3) have a cation exchanging equivalent (CEC) ratio of about 0.2~1.0. Phosphorus of HCP in the resin containing a flame retardant is 0.1~10 wt %. The intercalation reaction is controlled at 60~95° C.

In the present invention, the method for producing the resin containing a flame retardant includes a step of: (4) mixing the polymer with a phosphorous flame retardant to perform a cross-linking reaction, wherein the phosphorous flame retardant is produced by the method aforementioned. The cross-linking reaction is preferably controlled subsequently 20~30° C. (0.5~1.5 hours), 60~100° C. (0.5~1.5 hours) and 100~150° C. (4~6 hours); and more preferably subsequently about 25° C. (about 1 hours), about 80° C. (about 1 hours) and about 120° C. (about 5 hours). The phosphorous flame retardant is produced by the method aforementioned. The concentration of the layered silicate clays in the reactants is 0.1~15 wt %.

The above method can further comprise a cross-linker or curing agent, for example, diethyltriamine (DETA) or poly(oxyalkylene)-diamine or poly(oxyalkylene)-triamine having molecular weights ranging 200~1000. The equivalent ratio of the cross-linker or curing agent to poly(oxyalkylene)amine preferably ranges 1/10~10/1.

In the present invention, the poly(oxyalkylene)amine substitute is preferably poly(oxyalkylene)-diamine having molecular weight ranging 200~2500, for example, Jeffamine® D-amine series products, D230, D400 or D2000. The number N of the poly(oxyalkylene)amine substitute is preferably 3 or 6; and the structural formula of the phosphorous flame retardant is preferably as follows:

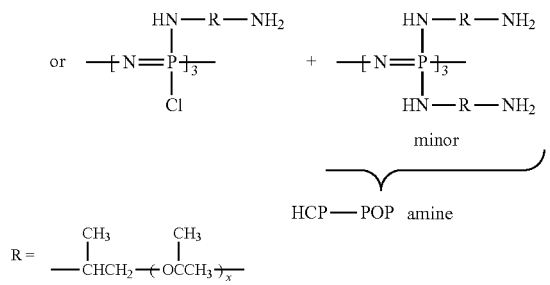

wherein the poly(oxyalkylene)amine substitute is poly(oxyalkylene)-diamine having molecular weight ranging 200~2500.

In the present invention, the layered silicate clay can be montmorillonite, bentonite, beidellite, nontronite, saponite, vermiculites, hectorite, volknerite, hydrotalcite, muscovite, biotite, attapulgite, talc, pyrophyllite or synthesized mica.

In the present invention, the polymer can be epoxy, polyethylene, polypropylene, polystyrene or ABS, wherein the epoxy can be epoxy having multiple functional groups, such as bisphenol A, diglycidyl ether of bisphenol A (DGEBA) epoxy, phenol formaldehyde novolac epoxy, or cresol formaldehyde novolac epoxy.

DETAILED DESCRIPTION OF THE PREFERRED EMBODIMENTS

Figure 1:
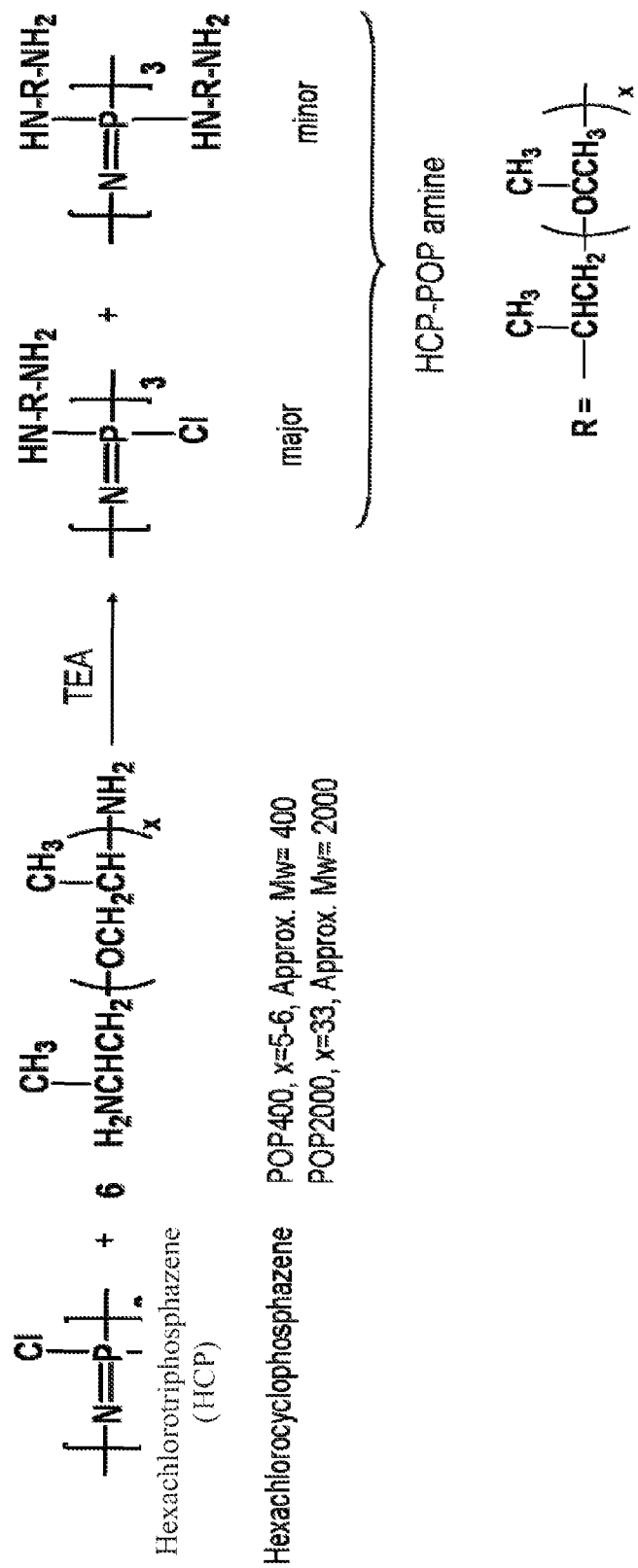
FIG. 1 shows the reaction of poly(oxyalkylene)amine and HCP to produce the flame retardant containing phosphorus.

FIG. 1 shows the reaction of the present invention. The —NH$_2$ end group can perform the ring-open reaction with epoxy to generate the thermosetting resin having better heat resistance.

The —NH$_2$ end group of the phosphazene-poly(oxyalkylene)amine adducts can be acidified into tertiary ammonia salts, and modified through the ionic exchanging reaction with cationic clay to obtain a composite flame retardant. Since properties such as mechanical strength, gas barrier and flame retardant, of polymers can be improved by binding with clay, the composite flame retardant is suitable for reacting with epoxy to obtain materials having good mechanical characteristics and flame retardant.

In the present invention, main materials used in Examples and Comparative Examples include:
(a) HCP: hexachlorocyclotriphosphazene (HCP), Mw=347.6 g/mole, merchandized from Kuo Ching Chemical Co., Ltd.

(b) montmorillonite: Na$^+$-MMT, cationic exchange equivalent (CEC)=120 meq/100 g, merchandized from Nanocor Co.

(c) triethylamine: triethylamine (TEA), Mw=101 g/mole, merchandized from Adrich; used for removing hydrochloric acid generated during a reaction; organic alkaline pyridine or inorganic alkaline NaOH being also suitable.

(d) poly(oxyalkylene)amine: poly(oxypropylene)-amines, merchandized from Hunstsman Chemical Co.; trademark Jeffamine® D-amine series; and having structural formula as follows:

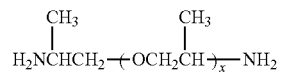

type: D230 (x=2~3); Mw~230 g/mole; also named POP-D230, type: D400 (x=5~6); Mw~400 g/mole; also named POP-D400, type: D2000 (x=33); Mw~2000 g/mole; also named POP-D2000.

(e) Diglycidyl ether of bisphenol A (DGEBA): merchandized from Nan Ya Plastics Co.; type: BE188; M$_w$=350; epoxy equivalent weight (EEW)=188; and having structural formula as follows:

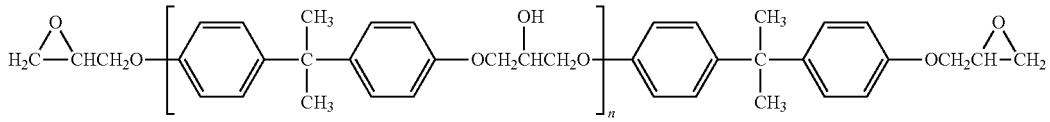

The detailed procedures for producing the flame retardant of the present invention are described as follow.

EXAMPLE 1

(1) Synthesizing the phosphazene-poly(oxyalkylene)amine Adduct

Tetrahydrofuran (THF, 40 g) and D400 (10 g, 25 mmole) were added in a three-necked bottle and uniformly mixed. HCP (7.24 g, 4.2 mmole, 20 wt % in THF) was slowly dropped into the above solution. Next, TEA (3.79 g) was slowly dropped into the three-necked bottle so that the mole ratio of HCP/D400/TEA was 1/6/9. The solution became white from transparency. The reaction was carried out in nitrogen gas, and controlled at 50° C. After 24 hours, the resultant salt was filtered with a filter paper and THF was removed by decompression rotary concentration to obtain the final product HCP-D400.

(2) Synthesizing the Resin Containing the Flame Retardant

BE188 (0.5 g), HCP-D400 (0.9 g) and D400 (0.089 g) were mixed with a homogenizer so that the equivalent ratio of BE188/HCP-D400/D400 was 1/0.5/0.5. The solution was poured in an alumina disk which was then placed in an oven for cross linking. The cross linking was performed at room temperature (1 hour), 80° C. (1 hour) and 120° C. (5 hours). The final product was BE188/HCP-D400.

EXAMPLE 2

(1) Synthesizing the phosphazene-poly(oxyalkylene)amine Adduct

Tetrahydrofuran (THF, 40 g) and D400 (10 g, 25 mmole) were added in a three-necked bottle and uniformly mixed.

HCP (7.24 g, 4.2 mmole, 20 wt % in THF) was slowly dropped into the above solution. Next, TEA (3.79 g) was slowly dropped into the three-necked bottle so that the mole ratio of HCP/D400/TEA was 1/6/9. The solution became white from transparency. The reaction was performed in nitrogen gas, and controlled at 50° C. After 24 hours, the resultant salt was filtered with a filter paper and THF was removed by decompress rotary concentration to obtain the final product HCP-D400.

(2) Synthesizing the Resin Containing the Flame Retardant

BE 188 (0.5 g) and HCP-D400 (1.8 g) were mixed with a homogenizer so that the equivalent ratio of BE188/HCP-D400 was 1/1. The solution was poured in an alumina disk which was then placed in an oven for cross linking. The cross linking was performed at 80° C. (1 hour) and 120° C. (5 hours). The final product was BE 188/HCP-D400.

EXAMPLES 3~4

Repeat steps (1) and (2) of Example 1, except that the equivalent ratios of BE188/HCP-D400/D400 were changed to 1/0.3/0.7 and 1/0.7/0.3, respectively.

COMPARATIVE EXAMPLE 1

Repeat step (2) of Example 1, except that HCP-D400 was not added so that the equivalent ratio of BE188/HCP-D400/D400 was 1/0/1.

EXAMPLE 5

(1) Synthesizing the phosphazene-poly(oxyalkylene)amine Adduct

Tetrahydrofuran (THF, 40 g) and D400 (10 g, 25 mmole) were added in a three-necked bottle and uniformly mixed. HCP (7.24 g, 4.2 mmole, 20 wt % in THF) was slowly dropped into the above solution. Next, TEA (3.79 g) was slowly dropped into the three-necked bottle so that the mole ratio of HCP/D400/TEA was 1/6/9. The solution became white from transparency. The reaction was performed in nitrogen gas, and controlled at 50° C. After 24 hours, the resultant salt was filtered with a filter paper and THF was removed by decompression rotary concentration to obtain the final product HCP-D400.

(2) Modifying MMT with the phosphazene-poly(oxyalkylene)amine Adduct

Water was added into a beaker containing $Na^+$-MMT (1 g, 1.2 meq.) to have a whole mass 100 g. The solution was then swollen at 80° C. for 1 hour. HCP-D400 (2.61 g, 3.6 meq.) from step (1) was mixed with $HCl_{(aq)}$ (0.125 g, 1.2 meq.) at an equivalent ratio ($H^+/—NH_2=1/3$) to acidify the $—NH_2$ end groups. Then the acidified HCP-D400 was added into the swollen MMT solution at an equivalent ratio (CEC/$H^+$/—$NH_2$=1/1/3) to perform ionic exchanging reaction. The ionic exchanging reaction was controlled at 80° C. for 3 hours. The product MMT/HCP-D400 (1/3) was precipitated and separated out from the solution.

(3) Synthesizing the Resin Containing a Flame Retardant

MMT/HCP-D400 (0.1 g) from step (2), D400 (1.667 g) and DGEBA (3.133 g) were mixed with a homogenizer. In the reactants, MMT had a concentration 1 wt %, and the equivalent ratio of DGEBA/D400 is 1/1. The solution was poured in an alumina disk which was then placed in an oven for cross linking. The cross linking was performed at room temperature (1 hour), 80° C. (1 hour) and 120° C. (5 hours). The final product was a nano-composite, DGEBA/MMT/HCP-D400.

EXAMPLES 6~8

Repeat steps (1)~(3) of Example 5, except that the contents of MMT were changed to 0.5 wt %, 3 wt % and 5 wt % (theoretical values), respectively; and the contents of phosphorus were changed to 0.02 wt %, 0.12 wt % and 0.2 wt %, respectively.

EXAMPLES 9~10

Repeat steps (1)~(2) of Example 5, except that HCP-D400 in step (2) was added in amounts of 0.435 g (0.6 meq.) and 0.87 g (1.2 meq.), respectively. The final products MMT/HCP-D400 were precipitated and separated out in equivalent ratios 1/0.5 and 1/1, respectively.

EXAMPLES 11~13

Repeat steps (1)~(2) of Example 5, except that HCP-D400 in step (2) was replaced with HCP-D2000 in amounts of 1.43 g (0.6 meq.), 2.86 g (1.2 meq.) and 8.59 g (3.6 meq.), respectively. The final products MMT/HCP-D2000 were precipitated and separated out in equivalent ratios 1/0.5, 1/1 and 1/3, respectively.

Analysis and Tests of the Products

1. Analysis of Molecular Weights and Structures

The products HCP-D400 and HCP-D2000 obtained in step 1 of Examples 1 and 13 were analyzed for determining molecular weights and amine titrations. For HCP-D400, the molecular weight was 1700 g/mol, the polydispersity index (PDI) of molecular weight was 2.49, and the titration value was 1.48 mequiv/g (theoretical value was 2.37 mequiv/g). For HCP-D2000, the molecular weights were 12,500 g/mol and 2,200 g/mol, the PDIs were 1.32 and 1.24, and the titration value was 0.42 mequiv/g (theoretical value was 0.49 mequiv/g). As this reaction is a substitution reaction with multiple reacting points, cross-linking reaction and steric hindrance would influence replacement of chlorine of HCP by D400 and D2000, and thus the products had branch-like structures.

2. Modification of MMT

Table 1 showed the interlayer distances (d spacing) of the products MMT/HCP-D400 and MMT/HCP-D2000 obtained in step 2 of Examples 5, 9-13. The interlayer distances increased from 1.26 nm up to 5.10 nm with the intercalatants (HCP-400 or HCP-D2000), and thus reactions could occur in nano regimes. Contents of the organic could increase to 70 wt %.

TABLE 1

| intercalatant | —$NH_3^+$/CEC | d spacing to (nm) | Content of organic (wt %) According TGA | Content of organic (wt %) According to CEC |
|---|---|---|---|---|
| none | — | 1.26 | — | — |
| HCP-D400/MMT | 0.5/1 | 2.35 | 29 | 35 |
|  | 1/1 | 2.67 | 37 | 52 |
|  | 3/1 | 3.56 | 52 | 76 |
| HCP-D2000/MMT | 0.5/1 | 4.64 | 66 | 71 |
|  | 1/1 | 4.80 | 68 | 83 |
|  | 3/1 | 5.10 | 70 | 94 |

3. Flame-Retarding Analysis of the Epoxy Films Containing HCP-D400

Figure 2:
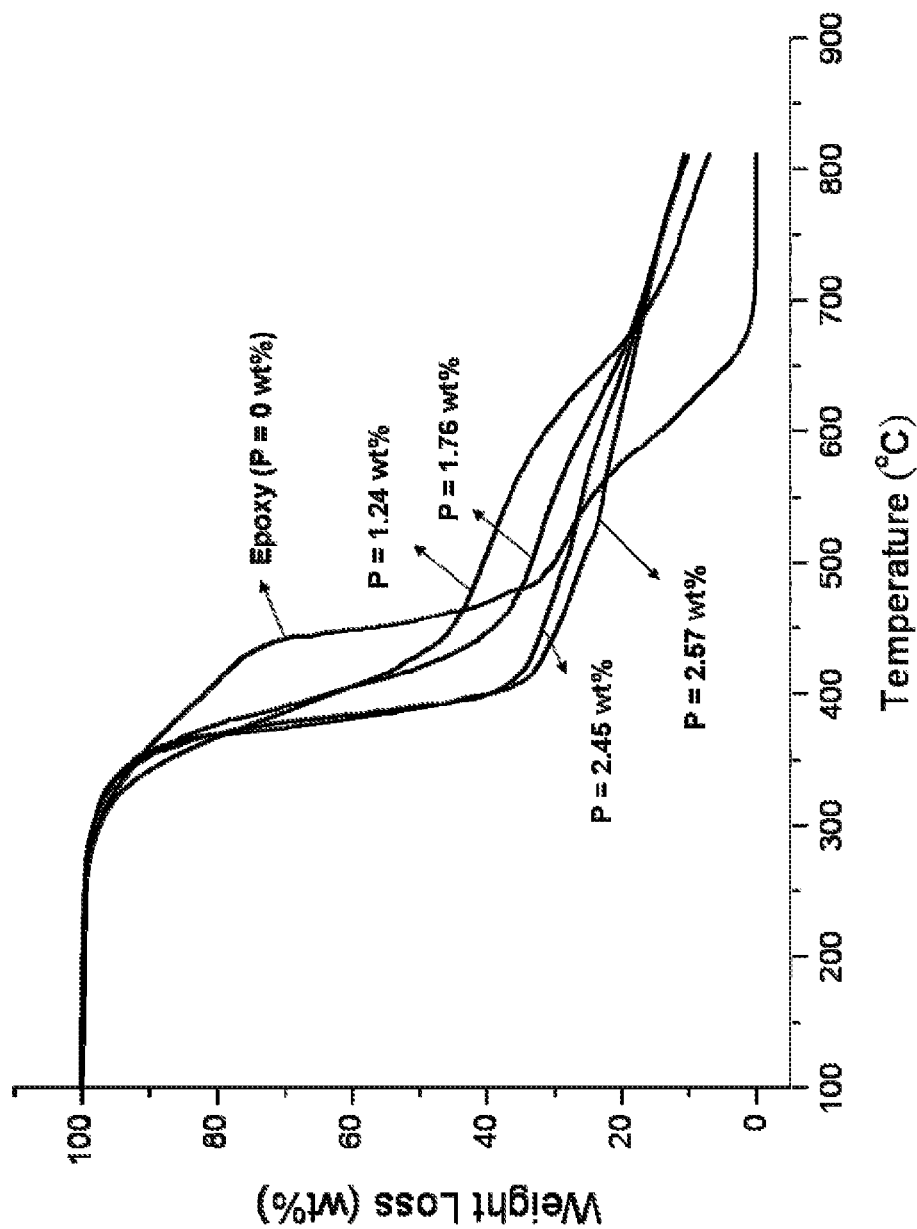
FIG. 2 shows the flame-retarding analysis of the film containing HCP-D400 epoxy.

The epoxy film (DGEBA/D400) of Comparative Example 1 and the epoxy films (DGEBA/HCP-D400/D400) of Examples 1~4 were used for TGA (thermal gravimetric analyses). Table 2 showed the results. For Comparative Example 1, $T_{10\ wt\%}$ (10 wt % of loss at this temperature) of the epoxy film decreased 4~18° C. with increasing ratios of the curing agent HCP-D400. With increasing of phosphorus, char yields due to cracking of the thermosetting epoxy films increased. The reason was that phosphorus of the triphosphorus nitride transformed to the phosphoric acid protective layer in cracking, which blocked oxygen off and prevented cracking. However, no D400 was added in Example 2, and thus the glass transition temperature (Tg) of the epoxy film decreased to 19° C. because of lower cross-linking density. FIG. 2 also showed such result.

TABLE 2

| Example/Comparative Example | DGEBA/HCP-D400/D400 (equivalent ratio) | Tg (° C.) | Content of phosphorous, calculated value (wt %) | Thermal stability | | Residual carbon at 800° C. (wt %) |
|---|---|---|---|---|---|---|
| | | | | $T_{10 wt\%}$ (° C.) | $T_{90 wt\%}$ (° C.) | |
| Example 1 | 1/0.5/0.5 | 30 | 1.76 | 353 | >800 | 11.1 |
| Example 2 | 1/1/0 | 19 | 2.57 | 354 | >800 | 11.0 |
| Example 3 | 1/0.3/0.7 | 32 | 1.24 | 342 | 768 | 7.8 |
| Example 4 | 1/0.7/0.3 | 28 | 2.45 | 356 | >800 | 11.2 |
| Comparative Example 1 | 1/0/1 | 48 | 0 | 360 | 622 | 0 |

4. Flame-Retarding Analysis of the Epoxy Films Containing MMT/HCP-D400

Figure 3:
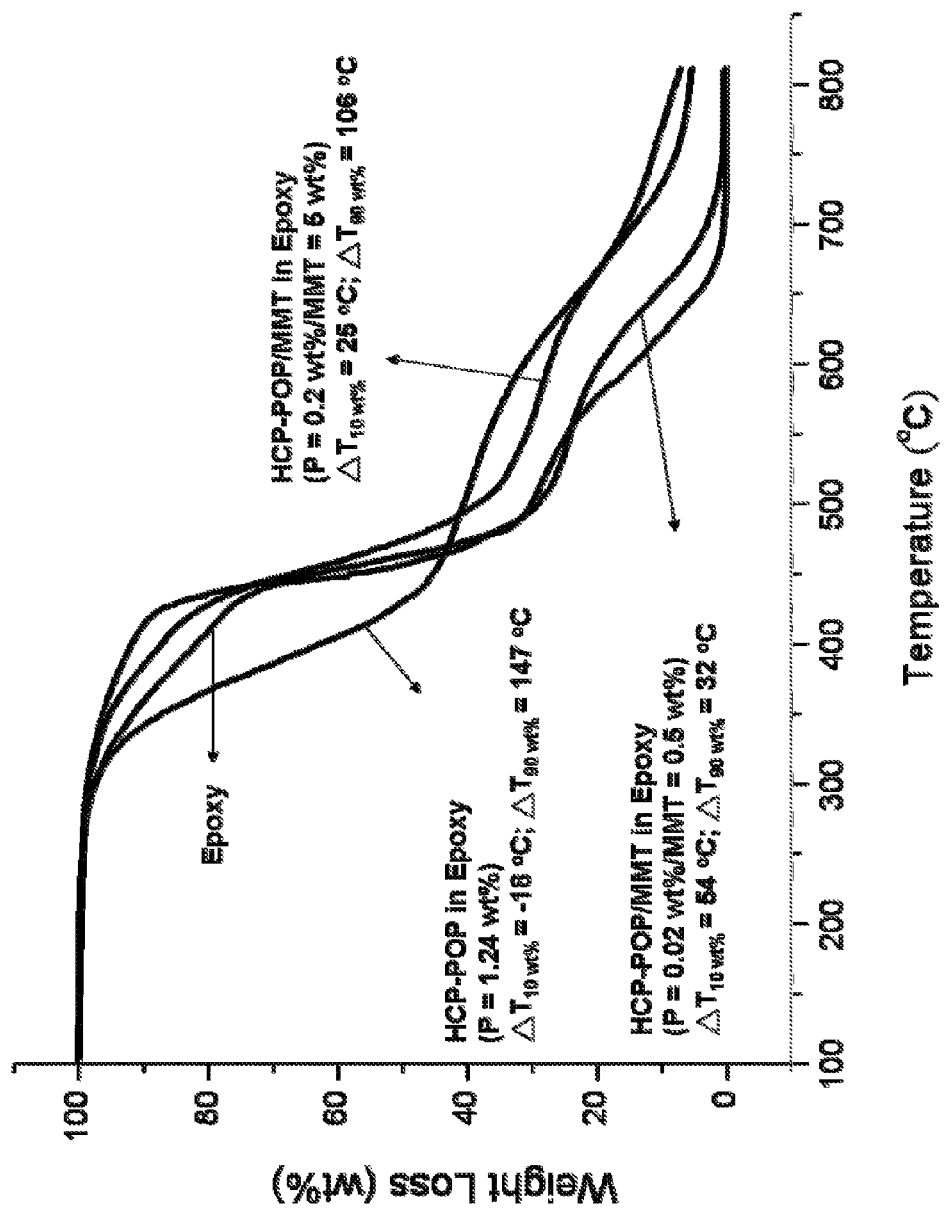
FIG. 3 shows the flame-retarding analysis of the film containing MMT/HCP-D400 epoxy.

The epoxy film (DGEBA/D400) of Comparative Example 1 and the epoxy films (DGEBA/MMT/HCP-D400/D400) of Examples 5~8 were used for TGA (thermal gravimetric analyses). Table 3 showed the results. When MMT was increased, thermal stability $T_{10wt\%}$ thereof increased by 25~54° C., and the second-staged cracking temperature $T_{90 wt\%}$ increased by 32~106° C. That is, by combining heat retardant of the inorganic layered MMT and flame retardant of phosphorus, thermal stability can be effectively promoted; wherein the MMT/HCP-D400 contained only 0.02~0.2 wt % of phosphorus. For Example 3, the epoxy film (DGEBA/HCP-D400/D400, content of phosphorus=1.24 wt %) contained no MMT, and FIG. 3 showed that $T_{10 wt\%}$ decreased by 18° C., and $T_{90 wt\%}$ increased by 146° C. When MMT/HCP-POP400 (MMT=5 wt %, phosphorus=0.2 wt %) was added into the epoxy, $T_{10 wt\%}$ increased by 25° C., and $T_{90 wt\%}$ increased by 106° C. That is, the flame-retarding MMT compensated instable phosphorus cracking at low temperature (300~500° C.). On the other hand, when cracking at high temperature, phosphorus generating the phosphoric acid protective layer and flame-retarding MMT facilitated thermal stability, better than HCP-D400 alone. In addition, increasing the inorganic layered clay also increased surface hardness of the epoxy by 2H.

TABLE 3

| Example/Comparative Example | Content of MMT (wt %) | | Content of phosphorous, calculated value (wt %) | Tg (° C.) | hardness | Thermal stability | |
|---|---|---|---|---|---|---|---|
| | Theoretical value | TGA value | | | | $T_{10 wt\%}$ (° C.) | $T_{90 wt\%}$ (° C.) |
| Example 5 | 1 | 0.8 | 0.04 | 35 | 4H | 391 | 677 |
| Example 6 | 0.5 | 0.4 | 0.02 | 42 | 3H | 414 | 654 |
| Example 7 | 3 | 3.0 | 0.12 | 37 | 5H | 382 | 710 |
| Example 8 | 5 | 5.5 | 0.20 | 42 | 5H | 385 | 727 |
| Comparative Example 1 | 0 | — | 0 | 48 | 3H | 360 | 622 |

According to the abovementioned, the phosphorous flame retardant of the present invention performed better by adding the phosphorous polymer. Furthermore, when combined with the flame-retarding inorganic layered clay, the thermal stability, flame retardant and mechanical characteristics of the nano composite can be promoted.

What is claimed is:

1. A method for producing phosphorous flame retardant, comprising steps of:
   (1) Mixing hexachlorocyclotriphosphazene (HCP), an alkaline and poly(oxyalkylene)amine in a solvent to perform a substitution reaction at 15-85° C. in which at least one chlorine of HCP is substituted by poly(oxyalkylene) amine having at least two —NH₂ end groups.

2. The method of claim 1, wherein the poly(oxyalkylene) amine is previously mixed in the solvent, then slowly dropped into HCP dissolved in the solvent, and then the alkaline is slowly dropped into the solvent.

3. The method of claim 1, wherein the reactants HCP and poly(oxyalkylene)amine have a molar ratio range from 1/1-1/12.

4. The method of claim 1, wherein the solvent is tetrahydrofuran (THF).

5. The method of claim 1, wherein the alkaline is triethylamine, pyridine or sodium hydroxide.

6. The method of claim 1, wherein the poly(oxyalkylene) amine is poly(oxyalkylene)-diamine having molecular weight from 200-2500 g/mol.

7. The method of claim 1, further comprising the steps after step (1):
   (2) mixing the product of the step (1) with an acid to acidify the —NH₂ end groups to —NH3$^+$;
   (3) mixing the acidified product of the step (2) with the layered silicate clay for intercalation reaction.

8. The method of claim 7, wherein the acid of the step (2) is hydrochloric acid, nitric acid or sulfuric acid.

9. The method of claim 7, wherein the —NH$_3^+$ to the layered silicate clay in the step (3) has a cation exchanging equivalent (CEC) ratio about 0.2-1.0.

10. The method of claim 7, wherein the intercalation reaction is operated at 60-95° C.

11. A method for producing a resin containing a flame retardant, comprising:
   uniformly mixing a polymer and a phosphorous flame retardant for cross-linking reaction, wherein the phosphorous flame retardant is produced by the method of claim 1.

12. The method of claim 11, wherein the polymer is epoxy, an acrylic resin, polyethylene, polypropylene, polystyrene or ABS.

13. The method of claim 11, wherein the HCP of the resin containing a flame retardant contains 0.1-10 wt % of phosphorus.

14. The method of claim 11, wherein the cross-linking reaction is operated at 20-30° C. for 0.5-1.5 hours, then 60-100° C. for 0.5-1.5 hours, and then 100-150° C. for 4-6 hours.

15. The method of claim 11, wherein the phosphorous flame retardant further comprises layered silicate clay in a concentration about 0.1-15 wt %.

16. The method of claim 11, further comprising a cross-linker.

17. The method of claim 16, the cross-linker is diethyltriamine (DETA) or poly(oxyalkylene)-diamine or poly(oxyalkylene)-triamine having molecular weight ranging from 20-1000 g/mol.

18. The method of claim 16, wherein the cross-linker to poly(oxyalkylene)amine has an equivalent ratio 1/10-10/1.

* * * * *